US00PP25232P3

(12) United States Plant Patent
Glen

(10) Patent No.: US PP25,232 P3
(45) Date of Patent: Jan. 20, 2015

(54) NECTARINE TREE NAMED 'PEARLICIOUS XXIII'

(50) Latin Name: *Prunus persica*
Varietal Denomination: Pearlicious XXIII

(71) Applicant: Lowell Glen, Le Grand, CA (US)

(72) Inventor: Lowell Glen, Le Grand, CA (US)

( * ) Notice: Subject to any disclaimer, the term of this patent is extended or adjusted under 35 U.S.C. 154(b) by 85 days.

(21) Appl. No.: 13/694,609

(22) Filed: Dec. 13, 2012

(65) Prior Publication Data

US 2014/0173789 P1 Jun. 19, 2014

(51) Int. Cl.
*A01H 5/00* (2006.01)

(52) U.S. Cl.
USPC ..... Plt./188

(58) Field of Classification Search
CPC ..... A01H 5/0856; A01H 5/00; A01H 5/08
USPC ..... Plt./188
See application file for complete search history.

(56) References Cited

U.S. PATENT DOCUMENTS

PP9,960 P 7/1997 Bradford
PP22,759 P2 5/2012 Bradford

*Primary Examiner* — June Hwu

(57) ABSTRACT

The present invention relates to a new and distinct variety of nectarine tree, *Prunus persica*, broadly characterized by a medium size, vigorous, hardy, self-fertile, productive and regular bearing tree. The variety blooms in the early to mid season and requires about 425 chilling hours. The fruit matures under the ecological conditions described in late May, with first picking on May 28, 2012. The fruit is uniformly medium in size, globose in shape, clingstone in type, firm and melting in texture, white in flesh color, full red in skin color, and a tasty balance of low acid and sugar in flavor.

1 Drawing Sheet

Botanical classification: *Prunus persica.*
Variety denomination: 'PEARLICIOUS XXIII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of nectarine tree, which has been denominated varietally as 'Pearlicious XXIII'.

In 2005 I made a first generation hybridization using 'Grand Pearl' (U.S. Plant Pat. No. 9,960) nectarine as the selected seed parent and '53P129' (unpatented) nectarine as the selected pollen parent. The fruit of this cross was gathered in the summer of 2005, and the seeds were removed from the fruit, germinated, stratified, and grown as seedlings on their own root in my greenhouse. Upon reaching dormancy that winter, the seedlings were transplanted as a group to a cultivated area of my experimental orchard located near Le Grand, Calif., in Merced County (San Joaquin Valley). During the fruit evaluation season of 2009 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its pollen parent, '53P129' by producing nectarines that are mostly red in skin color, but is quite distinguished therefrom by producing fruit that is white instead of yellow in flesh color, that is much less acidic in flavor, and that matures about ten days later.

The present variety is similar to its seed parent, 'Grand Pearl' (U.S. Plant Pat. No. 9,960) nectarine by being self-fertile and by producing white flesh clingstone nectarines that are firm, sweet, and full red skin color, but is quite distinguished therefrom by maturing about forty days earlier.

The present variety is most similar to 'Pearlicious II' (U.S. Plant Pat. No. 22,579) nectarine by blooming somewhat early, by being self-fertile, and by producing white flesh nectarines that have a bitter kernel and that are firm, sweet, and nearly full red in skin color, but is distinguished therefrom by having reniform instead of globose leaf glands and by producing fruit that is clingstone rather than freestone, that is somewhat smaller in size, and that matures about four days earlier.

SUMMARY OF VARIETY

In summary, the present nectarine variety is characterized by a medium size, vigorous, hardy, self-fertile, productive and regular bearing tree. The variety blooms in the early to mid season and requires about 425 chilling hours. The fruit matures under the ecological conditions described in late May, with first picking on May 28, 2012. The fruit is uniformly medium in size, globose in shape, clingstone in type, firm and melting in texture, white in flesh color, full red in skin color, and a tasty balance of low acid and sugar in flavor.

DRAWING

The accompanying photograph consists of four whole fruits positioned to display the characteristics of the skin color and form, one divided fruit to reveal the flesh and stone, three insets to reveal buds and a blossoms, a typical tip shoot, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of full ripe on Jun. 8, 2012, on the original tree during its seventh growing season. The blossom and flower descriptions were made the previous blooming season. All major color code designations are by reference to the Inter-Society Color Council, National Bureau of Standards. Common color names are also used occasionally.

PARENTAGE

Seed parent: 'Grand Pearl' nectarine (U.S. Plant Pat. No. 9.960).

Pollen parent: '53P129' nectarine (unpatented).

TREE

Size: Medium, reaching and maintaining a height of 9' [2.74 m.] and a spread of 6' [1.83 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 425 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

- *Size*.—Medium, reaching a maximum diameter of 3" [76.2 mm.] after the seventh growing season.
- *Texture*.—Medium shaggy.
- *Bark color*.—A Grayish brown [61. gy.Br] and Light grayish brown [60. l.gy.Br] variegation with Dark orange yellow [72. d.OY] crevices.
- *Lenticels*.—Approximate Number Per Square Inch: 7. Color: Brownish orange [54. brO]. Average Size: ¼" [6.4 mm.]. Shape: Eye-shaped, elongated.

Branches:

- *Size*.—Diameter of main scaffold is 2" [50.8 mm.] measured 12" above the crotch, diameter of limb is 1½" [38.1 mm.] measured 12" above the first fork.
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. Second Year Wood: Light grayish brown [60. l.gy.Br] with Strong brown [55. s.Br] permeating through.
- *Lenticels*.—Number Per Square Inch: About 50 on second year wood. Color: Brownish orange [54. brO]. Average size: 1/16" [1.6 mm.] on second year wood. Shape: Eye-shaped, elongated.

Leaves:

- *Size*.—Large. Average Length: 5" [127.0 mm.]. Average Width: 1½" [38.1 mm.].
- *Arrangement*.—Alternate.
- *Thickness*.—Medium.
- *Form*.—Elliptical.
- *Apex*.—Acuminate.
- *Base*.—Acute to rounded.
- *Surface*.—Smooth.
- *Color*.—Dorsal Surface: Moderate olive green [125. m.OlG]. Ventral Surface: Moderate yellow green (120. m.YG).
- *Margin*.—Finely serrate.
- *Venation*.—Pinnately net veined.
- *Vein color*.—Light yellow green [119. l.YG].
- Petiole.—Average Length: ½" [12.7 mm.]. Average Thickness: 1/16" [1.6 mm.]. Color: Very yellow green [115. v.YG] topside and a Brilliant yellow green [116. brill.YG] underside.
- *Stipules*.—Number: Usually 2 per leaf, up to 6 per growing tip. Average Length: ⅜" [9.5 mm.]. Color: Very yellow green [115. v.YG] becoming Moderate reddish brown [43. m.rBr] with maturity.
- *Glands*.—Number: 1 to 6 per leaf. Position: Alternate, located on the petiole and sometimes continued on the base of blade. Size: Medium. Form: Reniform. Color: Strong yellow green [117. s.YG] becoming Deep yellowish brown [75. deep yBr] with age.
- *Leaf buds*.—Pointed, medium in size.

Flower buds:

- *Hardiness*.—Hardy, with respect to central California winters.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Grayish purplish pink [253. gy.pPk].

Flowers: Perfect, complete, perigynous, usually a single pistil, about thirty stamens, five sepal and petal locations alternately positioned.

- *Type*.—Showy, large.
- *Average flower diameter*.—1 15/16" [49.2 mm.].
- *Number of petals*.—Mostly five, extra petal fragments or double blossoms are sometimes observed.
- Petal shape.—Circular to oval.
- Petal margin.—Entire, slightly wavy.
- *Average petal diameter*.—¾" [19.1 mm.].
- *Average petal length*.—¾" [19.1 mm.].
- *Petal apex*.—Rounded.
- *Petal base*.—Rounded to somewhat truncate.
- *Petal color*.—Pale pink [7. p.Pk] toward the apex, Deep purplish pink [248. deep pPk] toward the base on both sides.
- *Anther color*.—Moderate red [15. m.R] over a Light yellow [86. l.Y] center at bloom onset.
- *Pollen*.—Anthers produce an abundance of Brilliant yellow {83. brill.Y} pollen.
- *Stigma color*.—Pale yellow green [121. p.YG].
- *Stigma position*.—Typically located about even with the longest anthers.
- *Ovary*.—Non-pubescent.

*Sepal color*.—Dark purplish red [259. d.pR] on the outer surface.
*Sepal length*.—5/16" [7.9 mm.].
*Sepal width*.—3/16" [4.8 mm.].
*Sepal apex*.—Rounded to elliptical to match the sepal length and width.
*Sepal margin*.—Fairly smooth.
*Average pistil length*.—¾" [19.1 mm.].
*Average stamen length*.—⅝" [15.9 mm.].
*Fragrance*.—Moderate.
*Blooming period*.—Early to medium, five days before 'Spring Bright' (U.S. Plant Pat. No. 7,507) nectarine.
*Onset of bloom*.—One percent on Feb. 15, 2012.
*Date of full bloom*.—Feb. 24, 2012.
*Duration of bloom*.—One to two weeks, dependent on ambient temperature.
*Number per cluster*.—1 to 3 with single flowers most common.

FRUIT

Maturity when described: Full ripe, Jun. 8, 2012.
Date of first picking: May 28, 2012.
Date of last picking: Jun. 8, 2012.
Size: Uniform, medium.
*Average diameter axially*.—2½" [63.5 mm.].
*Average diameter across cheek plane*.—2⅝" [66.7 mm.].
*Average diameter across suture plane*.—2 9/16" [65.1 mm.].
*Typical weight*.—5.2 ounces [147.4 grams].
Form: Uniform, globose, compressed axially, slightly asymetrical.
*Longitudinal section form*.—Oblate.
*Transverse section through diameter*.—Round, slightly elongated toward the suture.
Suture: Extends from the base, continues along the side, and ends just past the pistil point.
*Near the base*.—A shallow groove.
*Along the side*.—A shallow trough.
*Near the apex*.—A shallow groove.
Ventral surface: Rounded, lipped toward the apex on both sides.
Lips: Slightly unequal.
Cavity: Flaring, slightly elongated in the suture plane, suture showing on one side, Pale orange yellow [73. p.OY] stem markings typical.
*Depth*.—7/16" [11.1 mm.].
*Breadth*.—⅞" [22.2 mm.].
Base: Rounded to truncate, slightly cordate if viewed parallel to the suture.
Apex: Cordate if viewed parallel to the suture.
Pistil point: An inconspicuous Dark brown [59. d.Br] dot, negligible in length, depressed within the suture.
Stem: Medium.
*Average length*.—⅜" [9.5 mm.].
*Average width*.—3/16" [4.8 mm.].
Skin:
*Thickness*.—Medium.
*Surface*.—Smooth.
*Tenacity*.—Tenacious to flesh.
*Astringency*.—Nonastringent.
*Tendency to crack*.—None observed in a dry season.
*Color*.—Dark red [16. d.R] over a Moderate red [15. m.R] background with minor Light orange yellow [70. l.OY] freckling mostly toward the apex.
Flesh:
*Color*.—Yellowish white [92. yWhite] throughout with Dark pink [6. d.Pk] flecking throughout.
*Surface of pit cavity*.—Covered with Pale yellow [89. p.Y] broken fibers when twisted from the stone.
*Amygdalin*.—Scarce.
*Juice*.—Moderate, rich.
*Texture*.—Firm, crisp, melting.
*Fibers*.—Abundant, fine.
*Ripens*.—Fairly even, slightly earlier at the apex.
*Flavor*.—A nice balance of light acid and sugar, typically 16 to 18 brix.
*Aroma*.—Slight.
*Eating quality*.—Very good.

STONE

Type: Clingstone.
Form: Oval.
Hilum: Narrow.
Base: Rounded, oblique.
Apex: Rounded with tip.
Sides: Equal.
Surface: Irregularly furrowed near the apex, pitted toward he base.
Ridges: Rounded.
External color: Dark orange yellow [72. d.OY].
Pit wall color when cracked: Light orange yellow [70. l.OY].
Cavity surface color: Moderate orange yellow [71. m.OY].
Average pit wall thickness: ¼" [6.4 mm.].
Average width: 15/16" [23.8 mm.].
Average length: 1¼" [31.8 mm.].
Average breadth: ¾" [19.1 mm.].
Tendency to split: None observed.
Kernel:
*Form*.—Oval.
*Skin color*.—Pale orange yellow [73. p.OY] when first removed.
*Pellicle color*.—Dark yellowish brown [78. d.yBr].
*Vein color*.—Moderate orange yellow [71. m.OY].
*Taste*.—Bitter.
*Viable*.—Yes.
*Average width*.—⅜" [9.5 mm.].
*Average length*.—⅝" [15.9 mm.].
*Amygdalin*.—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Pearlicious II' (U.S. Plant Pat. No. 22,579) nectarine by blooming somewhat early, by being self-fertile, and by producing white flesh nectarines that have a bitter kernel and that are firm, sweet, and nearly full red in skin color, but is distinguished therefrom by having reniform instead of globose leaf glands and by producing fruit that is clingstone rather than freestone, that is somewhat smaller in size, and that matures about four days earlier.

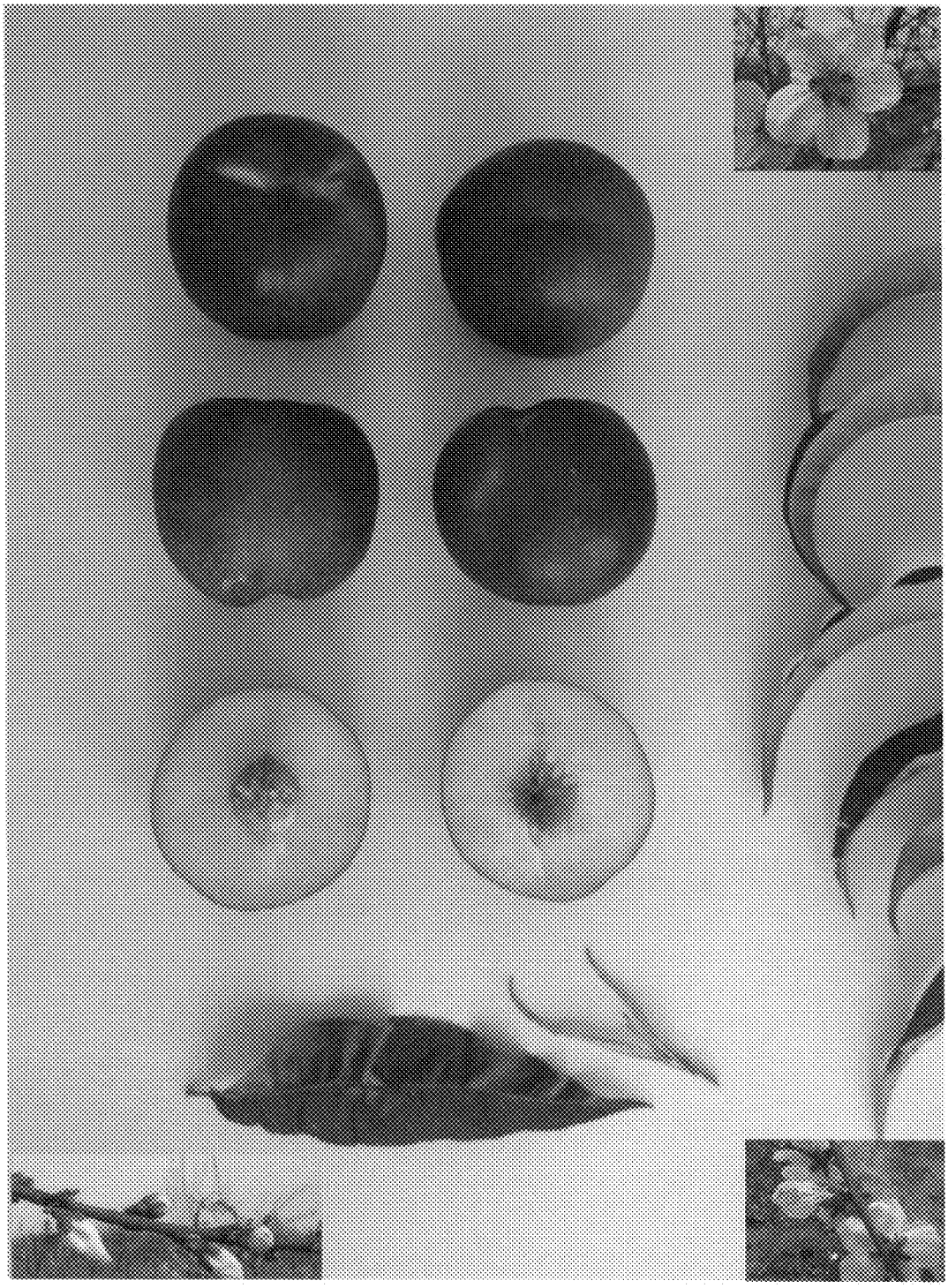

* * * * *